(12) United States Patent
Meehan

(10) Patent No.: US 7,981,406 B2
(45) Date of Patent: *Jul. 19, 2011

(54) COMPOSITIONS FOR ACCELERATING THE PRODUCTION OF COLLAGEN-CONTAINING PROTEINS

(76) Inventor: Kevin Meehan, Jackson, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/723,457

(22) Filed: Mar. 12, 2010

(65) Prior Publication Data

US 2010/0166883 A1    Jul. 1, 2010

Related U.S. Application Data

(63) Continuation-in-part of application No. 11/462,347, filed on Aug. 3, 2006, now Pat. No. 7,700,083.

(60) Provisional application No. 61/255,820, filed on Oct. 28, 2009, provisional application No. 60/729,880, filed on Oct. 24, 2005.

(51) Int. Cl.
*A61K 38/39* (2006.01)
*A61K 31/716* (2006.01)
*A61K 33/34* (2006.01)
*A61K 8/65* (2006.01)
*A61K 31/315* (2006.01)

(52) U.S. Cl. ......... 424/70.14; 424/638; 514/12; 514/54; 514/494; 562/433

(58) Field of Classification Search ............... 424/70.14, 424/638; 514/12, 54, 494; 562/433
See application file for complete search history.

(56) References Cited

U.S. PATENT DOCUMENTS

| | | | |
|---|---|---|---|
| 6,270,750 B1 * | 8/2001 | Dioguardi | 424/54 |
| 7,700,083 B2 * | 4/2010 | Meehan | 424/70.14 |
| 7,914,774 B2 * | 3/2011 | Meehan | 424/70.14 |

* cited by examiner

*Primary Examiner* — Chih-Min Kam
(74) *Attorney, Agent, or Firm* — Marger Johnson & McCollom, P.C.

(57) ABSTRACT

A composition includes ascorbate, zinc gluconate, and tropocollagen factors including L-proline, glycine and L-lysine. The composition contains the ascorbate, tropocollagen factors and zinc gluconate in concentrations effective to accelerate the production of collagen proteins within at least one collagen-containing tissue of an animal when administered to the animal. The at least one collagen-containing tissue includes at least one of cartilage tissue, tendon tissue, ligament tissue, vitreous humor tissue, connective tissue, hair tissue, bone tissue, and corneal tissue.

16 Claims, No Drawings

COMPOSITIONS FOR ACCELERATING THE PRODUCTION OF COLLAGEN-CONTAINING PROTEINS

CROSS-REFERENCE TO RELATED APPLICATIONS

The present application claims the benefit of U.S. Provisional Application No. 61/255,820, filed Oct. 28, 2009, which is incorporated herein in its entirety by reference. The present application is also a continuation-in-part of U.S. application Ser. No. 11/462,347, filed Aug. 3, 2006, now U.S. Pat. No. 7,700,083, which is a non-provisional application of U.S. Provisional Application No. 60/729,880, filed Oct. 24, 2005, each of which are incorporated herein in their entirety by reference.

BACKGROUND

1. Technical Field

This disclosure relates generally compositions formulated to accelerate the production of collagen proteins with an animal. More particularly, this disclosure relates to compositions formulated to accelerate the production of collagen-containing tissues of an animal that contain the collagen proteins.

2. Description of the Related Art

At least 12 different types of collagen exist within an animal's body, with Type I collagen being the most abundant. The basic triple-helix structure of Type I collagen is the prototype for most of the other collagen types. The other types of collagen differ from Type I collagen in the length of their triple helix and the presence or absence of globular domains at their amino or carboxyl terminal ends. Collagen itself is made up of a unique Amino Acid (AA) and Imino Acid (IA) composition with 33% of the total residues being glycine (Gly), 10% proline (Pro), 10% hydroxyproline (Hyp), and about 1% hydroxylysine (Hyl).

The basic structural unit of all types of collagen is tropocollagen, which is cross-linked to from large fibers of collagenous tissues. Tropocollagen is made of three polypeptide chains called α chains, where each of the α chains is wound around the other to form a triple helix structure. Every third AA or IA in the α chain is a glycine (hence the value of 33% for the relative amount of glycine present in collagen).

Sixty percent of the α chains are made of either the sequence Gly-Pro-X or the sequence Gly-X-Hyp, where X may be any AA or IA. The remaining forty percent of the α chains are various sequences of AAs and IAs, with every third AA or IA being a glycine. The AAs and IAs that compose tropocollagen may be referred to as tropocollagen factors.

A subset of particular proline and lysine residues in the region where the triple-helix formation occurs are hydroxylated before assembly can take place. Three enzymes are required for proper hydroxylation: lysl hydroxylase, prolyl-4-hydroxylase, and prolyl-3-hydroxylase.

Lysl hydroxylase converts lysines in the sequence X-Lys-Gly to 5-hydroxylysine. Prolyl-4-hydroxylase converts prolines in the sequence X-Pro-Gly to 4-hydroxyproline. Prolyl-3-hydroxylase converts prolines in the sequence Hyp-Pro-Gly to 3-hydroxyproline. The above hydroxylation reactions require ferrous/ferric iron, ascorbic acid (vitamin C), oxygen, and α-ketoglutarate in the chemical reaction that is described below in equation (1).

$$\text{AA or IA residue} + \text{iron} + \text{ascorbic acid} + O_2 + \alpha\text{-ketoglutarate} \rightarrow \text{hydroxyl-AA or IA} + \text{succinate} \quad (1)$$

Since the presence of new collagen proteins encourages the production of new collagen-containing tissues (e.g., cartilage tissue, tendon tissue, ligament tissue, hair tissue, etc.), the present inventor has found that it would be advantageous to develop compositions formulated to accelerate the production of new collagen proteins within an animal.

DETAILED DESCRIPTION OF EXAMPLE EMBODIMENTS

The inventor has recognized that the production of new collagen proteins may be advantageously accelerated by providing ascorbic acid (vitamin C) or a compound containing ascorbic acid, such as an ascorbate, and tropocollagen factors such as proline, glycine, and lysine, in ingestible and injectable compositions. As used herein, a tropocollagen factor refers to an amino- or imino-acid in its non-hydroxylated form. In some embodiments, the tropocollagen factors can be present as isolated amino-imino-acids, and not bound within one or more peptides. The ascorbic acid provided by the ingestible and injectable compositions disclosed herein enables the tropocollagen factors, which are also provided by the ingestible and injectable compositions disclosed herein, to be hydroxylated within the cells of the body which, in turn, accelerates the body's production of collagen proteins and consequently encourages the increased production of collagen-containing tissues such as cartilage (e.g., hyaline cartilage, elastic cartilage, and fibrocartilage), tendons, ligaments, hair, etc., within an animal (e.g., a human, a dog, a cat, a horse, etc.) when the composition is ingested by or injected into the animal. Production of collagen-containing tissues such as tendons and ligaments will occur faster when the composition is injected (e.g., intramuscularly or subcutaneously) into the animal as opposed to when the composition is ingested by the animal. Similarly, production of collagen-containing tissues such as hair will occur faster when the composition is applied topically to the hair of the animal as opposed to when the composition is ingested by the animal. Thus, the inventor recognizes that, compositions such as those exemplarily described in U.S. application Ser. No. 11/462,347 (which is incorporated by reference herein) can also be topically applied to existing hair tissue to accelerate the production of collagen-containing proteins therein.

In some embodiments, any of the compositions described in U.S. application Ser. No. 11/462,347 may additionally include threonine and/or serine. Each of these additional ingredients may be present at a minimum concentration of 0.001% m/v (or about 0.001% m/v), where "% m/v" denotes the mass of the ingredient when present as a solute in grams divided by the volume of solution in milliliters and multiplied by one hundred. There is no maximum concentration for either threonine or serine in the composition. In one embodiment, however, threonine may be present within the composition at a concentration of 1.31% m/v (or about 1.31% m/v). In another embodiment, serine may be present within the composition at a concentration of 3.33% m/v (or about 3.33% m/v).

The inventor has further recognized that, when topically applied to the skin of an animal, the compositions exemplarily described in U.S. application Ser. No. 11/462,347 exhibit an SPF of 14 when the skin was exposed to UV rays for approximately 15 minutes. The inventor is aware of some research suggesting that the REV 3 and REV 7 gene assists in the thymine-thymine dimmer response to DNA damage when exposed to UV rays. Glycine and L-lysine, as well as 2 additional amino acids, are not utilized by this gene. This could be one reason why burning/erythema is diminished upon UV exposure when the compositions exemplarily described in U.S. application Ser. No. 11/462,347 are applied to the skin.

When ingested or injected, the components in the composition exemplarily described herein meet the demand by the animal's body for the precursors necessary to produce specific collagen proteins incorporated within collagen-containing tissues at specific locations within the body. Thus, the compositions described herein can be used by the body to accelerate or initiate the formation of any type of collagen produced within the body (e.g., including Type I, Type II, Type III, Type IV, Type V, Type VI, Type VII, Type VII, Type IX, Type X, Type XI, etc.), depending on where it is applied (e.g., in the case where the composition is injected) and/or depending on the location(s) within the animal where demand for the components in the composition exists (e.g., in the case where the composition is ingested). Stated another way, all specialized cells located at specific sites in the body, which contribute to the formation of specific collagen types, can use the components in the compositions exemplarily described herein to initiate or sustain synthesis of collagen-containing tissues such as cartilage tissue, tendon tissue, ligament tissue, vitreous humor tissue, connective tissue, hair tissue, bone tissue, and corneal tissue. Compositions exemplarily described herein can be administered to repair damaged collagen-containing tissue or to maintain healthy collagen-containing tissue.

The inventor has further recognized that the presence of a transitional metal, such as copper, in an ingestible or injectable composition may be advantageously provided to ensure the proper function of the enzyme lysyl oxidase, which can be necessary for the cross-linking of collagen and elastin. Copper also helps to maintain equilibrium with zinc.

The inventor has further recognized that the presence of zinc in ingestible and injectable compositions containing a transitional metal such as copper synergistically provides maintenance of the integrity of biological membranes for protection against oxidative injury that might otherwise result from the elevated copper levels.

The above and other advantages associated with ingestible and injectable compositions according to embodiments of the invention are described in further detail below.

When expressing concentrations of a substance, the mass-volume percentage may be used for solutions made from solid reagents. For purposes of this disclosure, the mass-volume percentage, which is abbreviated as "% m/v," is defined as the mass of the solute in grams divided by the volume of solution in milliliters and multiplied by one hundred. The mass-volume percentage denotes the mass of the substance in a mixture as a percentage of the volume of the entire mixture.

Table IA lists some ingredients included in ingestible compositions according to some exemplary embodiments of the invention, as well as exemplary concentration ranges for those ingredients. As shown in Table IA, the ingestible composition may optionally include bioflavinoids, beta-1,3D-glucans, cysteine, alanine, and copper, or any combination thereof. In Table IA, the concentration ranges for the ingredients are given in mass-volume percentage (% m/v).

TABLE IA

| Component | Concentration range (% m/v) |
| --- | --- |
| L-Ascorbate | from 15 to 30 |
| L-Proline | from 3.33 |
| Glycine | from 3.33 |
| L-Lysine | from 1.31 |
| Copper (optional) | 0.5 to 5.0 |

TABLE IA-continued

| Component | Concentration range (% m/v) |
| --- | --- |
| Bioflavonoids (optional) | 0.5 to 1.5 |
| beta-1,3D-glucans (optional) | 0.05 to 0.15 |
| Cysteine (optional) | from 0.000001 |
| Alanine (optional) | from 0.000001 |
| Zinc gluconate | 0.01 to 0.03 |
| Silicon (optional) | 0.01 to 0.03 |

As shown in Table IA, the ingestible composition includes, at a minimum, 3.33% m/v (or about 3.33% m/v) of L-proline, 3.33% m/v (or about 3.33% m/v) of glycine and 1.31% m/v (or about 1.31% m/v) of L-lysine. There is no upper limit to the concentration of L-proline, glycine and L-lysine. An exemplary ingestible composition according to an exemplary embodiment of the invention includes the solutes listed below in Table IIA.

TABLE IIA

| Component | Concentration range (% m/v) |
| --- | --- |
| L-Ascorbate | 21.5 |
| L-Proline | 3.33 |
| Glycine | 3.33 |
| L-Lysine | 1.31 |
| Copper (optional) | 1.0 |
| Bioflavonoids (optional) | 1.0 |
| beta-1,3D-glucans (optional) | 0.1 |
| Cysteine (optional) | 0.5 to 2 |
| Alanine (optional) | 0.5 to 2 |
| Zinc gluconate | 0.021 |
| Silicon (optional) | 0.02 |

To obtain the ingestible composition as a liquid solution, the components listed in Table IA or IIA are provided as solutes which are blended in any suitable solvent (e.g., distilled water). The ingestible composition may also be prepared as a solid (e.g., as a power or tablet), according to any known technique.

Table IB lists some ingredients included in an injectable composition (e.g., via intramuscular injection or subcutaneous injection) according to some embodiments, as well as exemplary concentration ranges for those ingredients. As shown in Table IB, the injectable composition may optionally include bioflavinoids, cysteine, alanine, copper, or a combination thereof. In one embodiment, the injectable composition does not include beta-1,3D-glucans.

TABLE IB

| Component | Concentration range (% m/v) |
| --- | --- |
| L-Ascorbate | 15 to 30 |
| L-Proline | 2 to 5 |
| Glycine | 2 to 5 |
| L-Lysine | 0.5 to 2 |
| Copper (optional) | from 0.000001 |
| Bioflavonoids (optional) | 0.5 to 1.5 |
| Cysteine (optional) | 0.5 to 2 |
| Zinc gluconate | 0.01 to 0.03 |
| Silicon (optional) | 0.01 to 0.03 |

An exemplary injectable composition according to an embodiment includes the solutes listed below in Table IIB. As shown in Table IIB, the injectable composition may optionally include copper, bioflavinoids, cysteine, and silicon or any combination thereof. In one embodiment, the injectable composition does not include beta-1,3D-glucans.

TABLE IIB

| Component | Concentration range (% m/v) |
|---|---|
| L-Ascorbate | 21.5 |
| L-Proline | 3.33 |
| Glycine | 3.33 |
| L-Lysine | 1.31 |
| Copper (optional) | 1.0 |
| Bioflavonoids (optional) | 1.0 |
| Cysteine (optional) | 1.31 |
| Zinc gluconate | 0.021 |
| Silicon (optional) | 0.02 |

To obtain the injectable composition as a liquid solution, the components listed in Table IB or IIB are provided as solutes which are blended in any suitable solvent of 5% alcohol solution consisting of alcohol (e.g., ethanol) and distilled water. It will be understood by those of skill in the art that the solvent need not be a 5% alcohol solution, the solvent may be pure distilled water, or a 3% alcohol solution, or a 7% alcohol solution. It will also be appreciated that other embodiments may utilize other suitable solvents as desired if, for example, the ratio of an ingredient (e.g., silicon) or if the amounts (not ratios) of the components (e.g., L-proline, glycine and L-lysine) in Tables IB or IIB changes.

It will be understood by those of skill in the art that additional ingredients may be added to the ingredients listed in Tables IA, IIA, IB and IIB without departing from the teachings of the invention. However, the compositions do not contain collagen. When present in an ingestible form, the compositions exemplarily described herein can help to repair damaged collagen-containing tissues or help maintain health collagen-containing tissues (e.g., by maintaining elevated levels of the components identified in Tables IA and IIA within the body). When present in an injectable form, the compositions exemplarily described herein can help to repair damaged collagen-containing tissues (e.g., by providing elevated levels of the components identified in Tables IB and IIB at or near sites where demand is present for the components identified in Tables IB and IIB).

In the following paragraphs, some of the chemical properties and the advantageous contributions associated with the ingredients listed in Tables IA, IIA, IB and IIB are described.

As indicated in Tables IA, IIA, IB and IIB, compositions for accelerated production of collagen proteins according to some embodiments of the invention include ascorbate. In the exemplary composition described in Tables IIA and IIB, the ascorbate amounts to 21.5% m/v (or about 21.5% m/v) of the composition.

Ascorbates are mineral salts of ascorbic acid, which is weakly acidic. Typically, ascorbates are powders that are manufactured by reacting ascorbic acid with mineral carbonates in aqueous solutions, venting the carbon dioxide, drying the reaction product, and then milling the dried product to the desired particle size. Some examples of mineral carbonates suitable for reaction with ascorbic acid to form ascorbates include calcium carbonate, potassium carbonate, sodium bicarbonate, and magnesium carbonate. According to embodiments of the invention, one ascorbate or several different ascorbates may be used in the ingestible composition.

Because ascorbates are dry solids, they may be easily stored and measured and this is one reason why they are ingredients for the embodiments specified in Tables IA, IIA, IB and IIB. It is understood that when the ascorbates are dissolved in solution, ascorbic acid is produced and may participate in the hydroxylation of tropocollagen factors as described in equation (1) above. In alternative embodiments of the invention, ingestible and injectable compositions may substitute ascorbic acid for the ascorbates or may use mixtures of both ascorbic acid and ascorbates.

As was explained above, ascorbic acid is critical to the hydroxylation of tropocollagen to form new collagen proteins. According to embodiments of the invention, the ingestible and injectable compositions include significantly increased amounts of ascorbic acid or ascorbates to obtain an improved composition for accelerated production of collagen proteins.

As indicated in Tables IA, IIA, IB and IIB, compositions for accelerated production of collagen proteins according to embodiments of the invention include glycine, L-lysine, and L-proline. In the exemplary composition described in Tables IIA and IIB, the glycine, lysine, and proline amount to 3.33% m/v (or about 3.33% m/v), 1.31% m/v (or about 1.31% m/v), and 3.33% m/v (or about 3.33% m/v), respectively.

Since glycine is the simplest AA in the body and is of major importance in the synthesis of proteins, the sequencing requirement of this substance for the alpha chains becomes readily apparent. In other words, the body's capability of synthesizing adequate amounts of glycine under stress loading may be of concern, particularly in the field of collagen protein generation.

The essential AA lysine participates in the biosynthesis of proteins and the residues that are not metabolized in the liver are transported to various tissues in the body, such as connective tissues. As was described above, the unique AA and IA composition of collagen includes hydroxylysine (Hyl), which is a modified form of lysine. In order to produce 5-hydroxylysine (Hyl) from the lysine residues in the sequence X-Lys-Gly through a hydroxylation process, the enzyme lysyl hydroxylase is required.

The IA proline is synthesized from glutamate, and in the modified form is recognized as hydroxyproline which is found in structural proteins. Of interest here is its role in tropocollagen. When activated by the enzyme prolyl-4-hydroxylase, the prolines in the sequence X-Pro-Gly are converted to 4-hydroxyproline. The enzyme Prolyl-3-hydroxylase converts prolines in the sequence Hyp-Pro-Gly to 3-hydroxyproline.

All three of the above reactions require ascorbic acid for their hydroxylation reactions to occur, and the ascorbic acid is readily available because of the amount of ascorbate in the ingestible and injectable compositions.

As indicated in Tables IA, IIA, IB and IIB, compositions for accelerated production of collagen proteins according to embodiments of the invention may further include copper, which is a transitional metal. In the exemplary composition described in Table IIA and Table IIB, the copper, when included, can total 1.0% m/v (or about 1.0% m/v) of the composition. According to some embodiments, copper may be omitted from the injectable composition, or may be included within the injectable composition, depending on the site in the animal where the composition is to be injected.

Redox cycling between cuprous ($Cu^+$) and cupric ($Cu^{2++}$) ions can generate a highly reactive oxygen species that is destructive to biological membranes. Some intracellular proteins, such as metallothionein, have protecting mechanisms that safeguard against the potential toxicity of the copper ions. These protective intracellular proteins may be referred to as copper chaperones, since they have the ability to bind with copper ions, preventing them from generating the destructive oxygen species.

The inventor has recognized that the potentially destructive presence of increased copper ions may be effectively counteracted by increasing the copper chaperones that are present. The mechanism for achieving this will be explained in further detail below.

It should also be noted that the enzyme lysyl oxidase, which is necessary for the cross-linking of both collagen and elastin, requires copper for its proper function. For the above reasons, copper may be advantageously included in the embodiments described in Tables IA, IIA, IB and IIB.

As indicated in Tables IA, IIA, IB and IIB, compositions for accelerated production of collagen proteins according to embodiments of the invention may further include bioflavonoid extracts. In the exemplary composition described in Tables IIA and IIB, the bioflavonoid extracts, when included, amount to 1.0% m/v (or about 1.0% m/v) of the composition.

Bioflavonoid extracts demonstrate a wide range of pharmacological activities. In particular, one class of bioflavonoids, the proanthocyanidins (which include the extracts from pine bark and grape seed), are known for increasing intercellular vitamin C levels and inhibiting the destruction of collagen. Thus, bioflavonoids in general, and proanthocyanidins in particular, are well-suited for embodiments of the invention due to their beneficial interaction with ascorbic acid and collagen.

Additionally, the inventor has recognized that because bioflavonoids exhibit a cyto-protective effect that reduces inflammation and protects tissues, they can be used to reinforce the natural cross-linking that forms the collagen matrix. For this additional reason, bioflavonoid extracts are advantageously included in the embodiments of the invention described in Tables IA, IIA, IB and IIB.

As indicated in Tables IA and IIA, compositions for accelerated production of collagen proteins according to embodiments of the invention may further include beta-1,3D-glucans. In the exemplary composition described in Table IIB, the beta-1,3D-glucans, when included, totals 0.1% m/v (or about 0.1% m/v) of the composition.

Beta-D-glucans, usually referred to as beta-glucans, comprise a class of non-digestible polysaccharides widely found in nature in such sources as oats, barley, yeast, bacteria, algae and mushrooms. In oats, barley and other cereal grains, they are located primarily in the endosperm cell wall. Beta-1,3D-glucans is a substance that is extracted from red yeast, and the "1,3" terminology indicates that the substance is soluble and flexible.

As indicated in Tables IA, IIA, IB and IIB, compositions for accelerated production of collagen proteins according to some embodiments may include cysteine, which participates in the post translational processing of collagen. Cysteine is an important donator of sulfides, and its residues participate in the crosslinking of collagen. In one embodiment, the ratio of cysteine within the compositions indicated in Tables IA, IIA, IB and IIB may correspond to the ratio of L-lysine in the composition. Cysteine may also participate in the thickening of keratin shafts. Keratins contain a high proportion of the smallest of the 20 amino acids, glycine, and the next smallest, alanine. Fibrous keratin molecules can twist into helical structures which form the foundation for hair tissue. Thus, when the ingestible composition includes cysteine, the composition may advantageously accelerate thickening of hair tissue.

As indicated in Tables IA and IIA, compositions for accelerated production of collagen proteins according to some embodiments may include alanine, which participates in the thickening of keratin shafts. In one embodiment, the ratio of alanine within the compositions indicated in Tables IA and IIA may correspond to the ratio of L-lysine in the composition.

As indicated in Tables IA, IIA, IB and IIB, compositions for accelerated production of collagen proteins according to embodiments of the invention further include zinc gluconate, which provides zinc. In the exemplary composition described in Tables IIA and IIB, the zinc gluconate totals 0.021% m/v (or about 0.021% m/v) of the composition.

In the compositions according to Tables IA, IIA, IB and IIB, zinc gluconate has been exploited for its outstanding role in the formation of "zinc fingers." A zinc finger is a structure which is 30 amino acids long and is tightly bound with an atom of zinc. Zinc fingers are known for their beneficial interaction with DNA to regulate the activity of genes. Furthermore, it has long been recognized that zinc is capable of maintaining the integrity of biological membranes by protecting them against oxidative injury. The element zinc also supports the synthesis and formation of the copper chaperone metallothionein.

For the above reasons, zinc gluconate is advantageously included in the embodiments described in Tables IA, IIA, IB and IIB. In alternative embodiments of the invention, other substances that encourage the formation of different copper chaperones may be used in place of, or in addition to, zinc gluconate. Likewise, other sources of zinc may be used in place of, or in addition to, zinc gluconate.

As indicated in Tables IA, IIA, IB and IIB, compositions for accelerated production of collagen proteins according to embodiments of the invention may further include silicon (e.g., in any suitable form such as colloidal silicic acid). In the exemplary composition described in Tables IIA and IIB, the colloidal silicic acid, when included, amounts to 0.02% m/v (or about 0.02% m/v) of the composition.

Silicon is required for the enzyme prolylhydroxylase, which participates in the formation of collagen-containing tissues (e.g., cartilage, tendons, ligaments, etc.). The enzyme also appears to be involved in the synthesis of both glycosaminoglycan and collagen. Since most of the silicon in the body is found in the connective tissue and not bound to plasma, evidence suggests its role in the formation collagen in bone, cartilage and other connective tissues to be favorable.

A person skilled in the art will be able to practice the embodiments exemplarily discussed herein, where numerous details have been set forth in order to provide a more thorough understanding of the inventive concepts exemplarily described herein. In other instances, well-known features have not been described in detail in order not to unnecessarily obscure embodiments of the invention.

For example, the embodiments listed in Tables IA and IB express minimum concentration limits for the ingredients listed in the Tables. However, it should be emphasized that even trace amounts of the ingredients listed in Tables IA and IB may achieve some of the beneficial effects described above, albeit much less dramatically. Thus, some embodiments of the invention may include one or more of the solutes listed in Tables IA and IB, but at a concentration that is much less than the minimum concentration limit expressed therein.

Similarly, the embodiments described in Tables IA and IB express a maximum concentration limit for the ingredients listed in the Tables. Typically, there is some upper bound where a law of diminishing returns seems to operate. That is, there typically exists an upper concentration limit, where increasing the concentration of a substance any further beyond that limit becomes potentially unsafe and/or surpasses the capability of the body or other reactants in the composition to effectively utilize the substance. Thus, some other embodiments of the invention may include one or more of the ingredients listed in Tables IIA and IIB, but at a concentration that is greater than the maximum concentration limit expressed therein.

As such, it should be recognized that the concentration ranges given in Tables IA and IB provided above represent exemplary ranges where each of the ingredients may achieve optimal results, and that the exemplary ranges do not strictly limit the concentration of ingredients in embodiments of the invention to the specified ranges. Likewise, the particular concentrations given in Tables IIA and IIB represent exemplary formulation within the exemplary ranges of Tables IA and IB, respectively. It will further be appreciated that the amounts of any of the ingredients listed in Tables IA, IIA, IB and IIB may be adjusted (e.g., increased or decreased) as desired depending on the condition of any existing collagen-containing tissue (e.g., cartilage, tendon, ligament, hair, etc.).

Embodiments exemplarily described herein may additionally be practiced in many different ways. For example, the act of preparing a composition according to Tables IA, IIA, IB or IIB above is considered to be embodiments of the invention, as is the act of administering the compositions prepared according to Tables IA, IIA, IB or IIB above to an animal (e.g., orally, or by intramuscular or subcutaneous injection, as described herein) to encourage the accelerated production of collagen proteins.

Similarly, the ingredients listed in Tables IA, IIA, IB and IIB, when present as solutes of a liquid solution, may be mixed together in the appropriate proportions prior to being added to a predetermined amount of solvent, that the individual solutes may be sequentially added to the solvent, or that the solutes may be added to the solvent using some combination of the two processes. Likewise, mixtures of ingredients or separately packaged ingredients according to Tables IA, IIA, IB or IIB that are pre-measured and ready for administration to an animal or to be mixed with a predetermined amount of solvent are also considered to be compositions according to embodiments of the invention.

As exemplarily described above, compositions such as those prepared according to Tables IB or IIB may be injected into the muscle or subcutaneous tissue of an animal. Injecting such compositions into the animal encourages the accelerated production of collagen proteins and accelerates or initiates the production of collagen-containing tissues (e.g., cartilage, tendons, ligaments, etc.) within the animal, depending upon the location where the composition is injected. For example, production of cartilage within any joint may be accelerated by means of direct application via injection (e.g., intramuscular or subcutaneous) of a composition prepared according to Tables IB or IIB at or in proximity of (e.g., within about 20 mm of) the joint capsule, joint surface, or other anatomical placement (e.g., rib). In another example, production of tendon or ligament tissue may be accelerated by means of direct application via injection (e.g., intramuscular or subcutaneous) of a composition prepared according to Tables IB or IIB into the tendon or ligament.

As exemplarily described above, compositions such as those prepared according to Tables IA or IIA may be ingested by or injected into an animal. Ingesting or injecting such compositions encourages the accelerated production of collagen proteins and, therefore, accelerates or initiates the production of collagen-containing tissues (e.g., cartilage, hair, etc.) within the animal. For example, the articular cartilage of the joints, such as the knee cartilage, is hyaline cartilage which consists of approximately 5% of chondrocytes (total volume) seeded in approximately 95% extracellular matrix (total volume). The extracellular matrix contains a variety of macromolecules including Type II collagen and proteoglycan. The structure of the hyaline cartilage matrix allows it to absorb shock and withstand shearing and compression forces reasonably well. Normal hyaline cartilage has also an extremely low coefficient of friction at the articular surface. Healthy hyaline cartilage has a contiguous consistency without any lesions, tears, cracks, ruptures, holes or shredded surface. Due to trauma, injury, disease (e.g., osteoarthritis, rheumatoid arthritis, etc.) or aging, however, the contiguous surface of the cartilage is disturbed and the cartilage surface shows cracks, tears, ruptures, holes or shredded surface resulting in cartilage lesions. Partly because hyaline cartilage is avascular, the spontaneous healing of large defects is not believed to occur in humans and other mammals and the articular cartilage has thus only a limited, if any, capacity for repair. Thus, production of hyaline cartilage tissue (e.g., at joints within an animal) may be accelerated by means of ingestion of a composition prepared according to Tables IA or IIA or by means of injection of a composition prepared according to Tables IB or IIB.

It should be appreciated that reference throughout this specification to "one embodiment" or "an embodiment" means that a particular feature, structure or characteristic described in connection with the embodiment is included in at least one embodiment of the invention. Therefore, it should be emphasized and appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

Similarly, it should be appreciated that in the foregoing description of exemplary embodiments of the invention, various features of the invention are sometimes grouped together in a single embodiment or description thereof for the purpose of streamlining the disclosure aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects may lie in less than all features of a single disclosed embodiment. Thus, the claims following this detailed description are hereby expressly incorporated into this detailed description, with each claim standing on its own as a separate embodiment of this invention.

Having described and illustrated the inventive aspects by describing and explaining several exemplary embodiments of the invention, it should be apparent that the embodiments may be modified in arrangement and detail without departing from such principles. I claim all modifications and variation coming within the spirit and scope of the attached claims.

The invention claimed is:

1. A liquid solution comprising:
   solutes comprising zinc gluconate and ascorbate and tropocollagen factors including L-proline, glycine and L-lysine; and
   a solvent,
   wherein the liquid solution contains the solutes in concentrations effective to accelerate the production of collagen proteins within an animal when applied to the animal via intramuscular or subcutaneous injection.

2. The liquid solution of claim 1, the ascorbate representing about 15 to about 30% m/v of the liquid solution.

3. The liquid solution of claim 1, the tropocollagen factors representing about 4.5 to about 12.0% m/v of the liquid solution.

4. The liquid solution of claim 1, the zinc gluconate representing about 0.01 to about 0.03% m/v of the liquid solution.

5. The liquid solution of claim 1, the solutes further comprising cysteine.

6. The liquid solution of claim 1, wherein the liquid solution does not include copper.

7. An ingestible composition, comprising:
ascorbate;
tropocollagen factors including L-proline, glycine and L-lysine;
copper; and
zinc gluconate,
wherein the composition contains the ascorbate, tropocollagen factors, copper and zinc gluconate in amounts effective to accelerate the production of collagen proteins within an animal when ingested by the animal.

8. The ingestible composition of claim 7, wherein the composition is a liquid.

9. The ingestible composition of claim 7, wherein the composition further comprises cysteine.

10. The ingestible composition of claim 7, wherein the composition further comprises alanine.

11. The ingestible composition of claim 7, wherein the ascorbate is about 15 to about 30% m/v of the liquid solution.

12. The ingestible composition of claim 7, wherein the tropocollagen factors are about 4.5 to about 12% m/v of the liquid solution.

13. The ingestible composition of claim 7, wherein the copper is about 0.5 to about 5.0% m/v of the liquid solution.

14. The ingestible composition of claim 7, wherein the zinc gluconate is about 0.01 to about 0.03% m/v of the liquid solution.

15. The ingestible composition of claim 7, wherein the composition does not comprise collagen.

16. A composition, comprising:
ascorbate;
tropocollagen factors including L-proline, glycine and L-lysine; and
zinc gluconate,
wherein the composition contains the ascorbate, tropocollagen factors and zinc gluconate in concentrations effective to accelerate the production of collagen proteins within at least one collagen-containing tissue of an animal when administered to the animal, and
wherein the at least one collagen-containing tissue including at least one selected from the group consisting of cartilage tissue, tendon tissue, ligament tissue, vitreous humor tissue, connective tissue, hair tissue, bone tissue, and corneal tissue.

* * * * *